(12) United States Patent
Maio et al.

(10) Patent No.: US 11,083,743 B2
(45) Date of Patent: Aug. 10, 2021

(54) DNA HYPOMETHYLATING AGENTS FOR CANCER THERAPY

(71) Applicants: Michele Maio, Roveredo in Piano (IT); Sandra Coral, Gorgo al Monticano (IT); Alessia Covre, Tavagnacco (IT)

(72) Inventors: Michele Maio, Roveredo in Piano (IT); Sandra Coral, Gorgo al Monticano (IT); Alessia Covre, Tavagnacco (IT)

( * ) Notice: Subject to any disclaimer, the term of this patent is extended or adjusted under 35 U.S.C. 154(b) by 0 days.

(21) Appl. No.: 14/767,743

(22) PCT Filed: Feb. 21, 2014

(86) PCT No.: PCT/EP2014/053397
§ 371 (c)(1),
(2) Date: Aug. 13, 2015

(87) PCT Pub. No.: WO2014/128245
PCT Pub. Date: Aug. 28, 2014

(65) Prior Publication Data
US 2015/0374731 A1    Dec. 31, 2015

Related U.S. Application Data

(60) Provisional application No. 61/767,517, filed on Feb. 21, 2013.

(51) Int. Cl.
| | |
|---|---|
| *A61K 31/706* | (2006.01) |
| *A61K 45/06* | (2006.01) |
| *A61K 31/7068* | (2006.01) |
| *A61K 39/395* | (2006.01) |
| *A61K 39/00* | (2006.01) |

(52) U.S. Cl.
CPC ........ *A61K 31/706* (2013.01); *A61K 31/7068* (2013.01); *A61K 39/39558* (2013.01); *A61K 45/06* (2013.01); *A61K 2039/505* (2013.01)

(58) Field of Classification Search
CPC .............. A61K 31/706; A61K 31/7068; A61K 2300/00; A61K 2039/505; A61P 35/00; A61P 35/02; A61P 35/04
See application file for complete search history.

(56) References Cited

U.S. PATENT DOCUMENTS

| | | | |
|---|---|---|---|
| 2002/0114809 A1 | 8/2002 | Rubinfeld et al. | |
| 2010/0222381 A1* | 9/2010 | Vankayalapati | A61K 31/381 514/312 |

FOREIGN PATENT DOCUMENTS

WO    WO-2008156712 A1 * 12/2008    ......... C07K 16/2803

OTHER PUBLICATIONS

Robinson, PLoS Biology, 2004, vol. 2, pp. 0018-0020.*
Klisovic et al (Clinical Cancer Research, 2008, vol. 14, pp. 2444-2449).*
Winquist et al (Investigational New Drugs, 2006, vol. 24, pp. 159-167).*
Chao et al (Cell, 2010, vol. 142, pp. 699-713).*
Hirata et al (Blood, 2009, vol. 113, pp. 4885-4893).*
Ansell et al (Clinical Cancer Research, 2009, vol. 15, pp. 6446-6453).*
ClinicalTrials.gov Archive, NCT00275080, version on Dec. 1, 2009.*
Clinical Trials.gov archive for NCT00612664 (version of Jan. 24, 2011). (Year: 2011).*
Clinical Trials.gov archive for NCT01561911 (version of Mar. 22, 2012). (Year: 2012).*
Clinical Trials.gov archive for NCT01103635 (version of Feb. 8, 2012). (Year: 2012).*
Clinical Trials.gov archive for NCT01644968 (version of Jul. 18, 2012) (Year: 2012).*
Clinical Trials.gov archive for NCT00729664 (version of Feb. 2, 2012) (Year: 2012).*
Clinical Trials.gov archive for NCT01098084 (version of Nov. 28, 2011). (Year: 2011).*
Coral et al (British Journal of Cancer, ePub: Aug. 21, 2012, vol. 107, pp. 1116-1124) (Year: 2012).*
Graziani et al (Pharmacological Review, 2012, vol. 65, pp. 9-22) (Year: 2012).*
Topalian et al (Current Opinion in Immunology, 2012, vol. 24, pp. 207-212) (Year: 2012).*
Abstract of Yang et al (Blood, Nov. 16, 2012, vol. 120, No. 21, p. 3810) (Year: 2012).*
Pardoll (Nature Reviews Cancer, 2012, vol. 12, pp. 252-263) (Year: 2012).*
Borthakur et al (Haematologica, 2011, vol. 96, pp. 62-68) (Year: 2011).*
Zhang etal (Leukemia, 2008, vol. 22, pp. 808-818) (Year: 2008).*
The abstract of Jain et al (Journal of Clinical Oncology, 2012, vol. 30, No. 15, suppl, abstract 6582) (Year: 2012).*
Nishioka et al, (Leukemia 2007, vol. 21, pp. 1308-1310) (Year: 2007).*
Park et al (BMB Reports, 2011, vol. 44, pp. 517-522) (Year: 2011).*
Abstract of Baselga et al (Cancer Research, 2009, vol. 69, No. 24, suppl. Abstract No. 45) (Year: 2009).*
Shi et al (Autophagy, 2011, vol. 7, pp. 1159-1172) (Year: 2011).*
Jensen et al (Seminars in Oncology, 2010, vol. 37, pp. 524-532) (Year: 2010).*
Demaria et al (Clinical Cancer Research, 2001, vol. 7, pp. 3025-3030) (Year: 2001).*
Weber et al (Current Opinion in Oncology, 2011, vol. 23, pp. 163-169) (Year: 2011).*
Daver, Naval, et al: "Decitabine and Gemtuzumab Ozogamicin in Acute Myelogenous Leukemia and High-Risk Myelodysplastic Syndrome", Blood, vol. 120, No. 21, Nov. 2012 (Nov. 2012), p. 3619; & 54th Annual Meeting and Exposition of the American-Society-of-Hematology (ASH); Atlanta, GA, USA; Dec. 8-11, 2012.

(Continued)

*Primary Examiner* — Karen A. Canella
(74) *Attorney, Agent, or Firm* — Lucas & Mercanti, LLP (57) ABSTRACT

The present invention relates to a method of treating and/or preventing cancer comprising administering a combination of an effective amount of a DNA hypomethylating agent and an effective amount of at least one immunomodulatory agent and/or optionally an effective amount of at least one targeted therapy agent.

26 Claims, 8 Drawing Sheets

Specification includes a Sequence Listing.

(56) References Cited

OTHER PUBLICATIONS

F. J. Reu, et al: "Overcoming Resistance to Interferon-Induced Apoptosis of Renal Carcinoma and Melanoma Cells by DNA Demethylation", Journal of Clinical Oncology, vol. 24, No. 23, Jun. 26, 2006 (Jun. 26, 2006), pp. 3771-3779.

D. K. Krishnadas, et al: "Complete Remission Following Decitabine/Dendritic Cell Vaccine for Relapsed Neuroblastoma", Pediatrics, vol. 131, No. 1, Dec. 24, 2012 (Dec. 24, 2012), pp. e336-e341.

L. Hambach, et al: "Hypomethylating drugs convert HA-1-negative solid tumors into targets for stem cell-based immunotherapy", Blood, vol. 113, No. 12, Jan. 23, 2009 (Jan. 23, 2009), pp. 27.

Maio, M., et al: "Epigenetic Targets for Immune Intervention in Human Malignancies", Oncogene, Nature Publishing Group, GB, vol. 22, No. 42, Sep. 29, 2003 (Sep. 29, 2003), pp. 6484-6488.

Steven J. O'Day, et al: "Targeting cytotoxic T-lymphocyte antigen-4 (CTLA-4)", Cancer, vol. 110, No. 12, Dec. 15, 2007 (Dec. 15, 2007), pp. 2614-2627.

Leach, D. R., et al: "Enhancement of Antitumor Immunity by CTLA-4 Blockade", Science, American Association for the Advancement of Science, US, vol. 271, Mar. 22, 1996 (Mar. 22, 1996), pp. 1734-1736.

H Yang: "Paper: Induction of PD-1 and PD-1 Ligand Expression by Hypomethylating Agents (HMA) in Myelodysplastic Syndromes and Acute Myelogenous Leukemia Suggest a Role for T Cell Function in Clinical Resistance to Hmas", Dec. 10, 2012 (Dec. 10, 2012), Retrieved from the Internet: URL:https://ash.confex.com/ash/2012/webprogram/Paper54064.html [retrieved on Mar. 24, 2014].

H Yang, et al: "Expression of PD-L1, PD-L2, PD-1 and CTLA4 in myelodysplastic syndromes is enhanced by treatment with hypomethylating agents", Leukemia, Nov. 25, 2013 (Nov. 25, 2013).

Weber, "Immune Checkpoint Proteins: A New Therapeutic Paradigm for Cancer—Preclinical Background: CTLA-4 and PD-1 Blockade", Seminars in Oncology, 2010, vol. 37, No. 5, pp. 430-439.

Topalian et al., "Safety, Activity, and Immune Correlates of Anti—PD-1 Antibody in Cancer", The New England Journal of Medicine, 2012, vol. 366, No. 26, pp. 2443-2454.

O'Day et al., "Targeting Cytotoxic T-Lymphocyte Antigen-4 (CTLA-4) A Novel Strategy for the Treatment of Melanoma and Other Malignancies", Cancer, 2007, vol. 110, No. 12, pp. 2614-2627.

Loke et al., "PD-L1 and PD-L2 are differentially regulated by Th1 and Th2 cells", PNAS, 2003, vol. 100, No. 9, pp. 5336-5341.

Iwai et al., "Involvement of PD-L1 on tumor cells in the escape from host immune system and tumor immunotherapy by PD-L1 blockade", PNAS, 2002, vol. 99, No. 19, pp. 12293-12297.

Hodi et al., "Improved Survival with Ipilimumab in Patients with Metastatic Melanoma", N Engl J Med., 2010, vol. 362, No. 8, pp. 711-723.

Di Giacomo et al., "Ipilimumab experience in heavily pretreated patients with melanoma in an expanded access program at the University Hospital of Siena (Italy)", Cancer Immunol Immunother, 2011, vol. 60, pp. 467-477.

Brahmer et al., "Safety and Activity of Anti-PD-L1 Antibody in Patients with Advanced Cancer", The New England Journal of Medicine, 2012, vol. 366, No. 26, pp. 2455-2465.

Mastrangelo et al, Ed. "Immunologic Checkpoints for Cancer Treatment: From Scientific Rationale to Clinical Application", Seminars in Oncology, 2010, vol. 37, No. 5, pp. 419-547, and particularly pp. 429-547.

* cited by examiner

SEQUENCE LISTING

<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: synthetic primer

<400> SEQUENCE: 1
ggtgccggag ctgagga                                                17

<210> SEQ ID NO 2
<211> LENGTH: 23
<212> TYPE: DNA
<213> ORGANISM: Artificial Sequence
<220> FEATURE:
<223> OTHER INFORMATION: synthetic primer

<400> SEQUENCE: 2
tagacaccag gaaattaggg tcg                                         23

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
accagttcgc catggatgac                                             20

<210> SEQ ID NO 4
<211> LENGTH: 16
<212> TYPE: DNA
<213> ORGANISM: Artificial Sequence
<220> FEATURE:
<223> OTHER INFORMATION: synthetic primer

<400> SEQUENCE: 4
tgccggagcc gttgtc                                                 16

<210> SEQ ID NO 5
<211> LENGTH: 29
<212> TYPE: DNA
<213> ORGANISM: Artificial Sequence
<220> FEATURE:
<223> OTHER INFORMATION: synthetic primer

<400> SEQUENCE: 5
ttaagtgcgt tattacgttt ggtttttac                                   29

<210> SEQ ID NO 6
<211> LENGTH: 30
<212> TYPE: DNA
<213> ORGANISM: Artificial Sequence
<220> FEATURE:
<223> OTHER INFORMATION: synthetic primer

<400> SEQUENCE: 6
ataaccgatt atttaataca aaaatcgacg                                  30

<210> SEQ ID NO 7
<211> LENGTH: 31
<212> TYPE: DNA
<213> ORGANISM: Artificial Sequence

```
<220> FEATURE:
<223> OTHER INFORMATION: synthetic primer

<400> SEQUENCE: 7
gattaagtgt gttattatgt ttggttttta t                            31

<210> SEQ ID NO 8
<211> LENGTH: 32
<212> TYPE: DNA
<213> ORGANISM: Artificial Sequence
<220> FEATURE:
<223> OTHER INFORMATION: synthetic primer

<400> SEQUENCE: 8
acataaccaa ttatttaata caaaaatcaa ca                           32
```

DNA HYPOMETHYLATING AGENTS FOR CANCER THERAPY

CROSS-REFERENCE TO RELATED APPLICATIONS

The present application is a 371 of PCT/EP2014/053397, filed Feb. 21, 2014, which claims the benefit of U.S. Provisional Patent Application No. 61/767,517, filed Feb. 21, 2013.

FIELD OF THE INVENTION

The present invention relates to a method of treating and/or preventing cancer comprising administering a combination of an effective amount of a DNA hypomethylating agent and an effective amount of at least one immunomodulatory agent and/or optionally an effective amount of at least one targeted therapy agent.

BACKGROUND ART

Pre-clinical in vitro and in vivo evidences largely contributed to identify alterations in DNA methylation occurring in cancer cells, as a major mechanism impairing their immunogenicity and immune recognition. However, DNA hypomethylating agents (DHA) have been shown to be able to restore the altered immune profile of cancer cells, through a positive modulation of different immune molecules (e.g., Cancer Testis Antigens (CTA), HLA antigens, accessory/co-stimulatory molecules), directly involved in cellular and humoral immune recognition of cancer cells (Sigalotti L, et al. Semin Oncol. 2005; 32:473-8; Coral S, et al. J Cell Physiol. 2006; 207:58-66; Fratta E, et al. J Cell Physiol. 2010; 223:352-8). These immunomodulatory properties of DHA strongly suggest for their potential clinical application in setting up novel therapeutic strategies in cancer, either when utilized as single agent, or in combination with different immunotherapeutic agents. Among these, the growing family of therapeutic immunomodulating monoclonal antibodies (mAb) represent optimal candidates for combination therapies with DHA. Several immunomodulating mAb that target cell membrane molecules expressed on immune cells are already available (e.g., anti-CTLA-4, -PD1, -PDL1, -CD137, OX-40, CD40) (Seminars in Oncology, 2010 37:429-547) and are being developed in clinical trials in different cancer histotypes. The prototype of these immunomodulating agents are the anti-CTLA-4 mAb that represent novel therapeutic tools that can be effectively utilized to up-regulate anti-cancer immune responses by blocking inhibitory pathways of T-cell activation (O'Day S J, et al. Cancer 2007; 110:2614-2627). Blockade of CTLA-4 signaling has been shown to induce tumor rejection in animal models, (Leach D R, et al. Science 1996; 271:1734-1736; Weber J, Semin Oncol 2010; 37:430-439) and has been proved effective in inducing long lasting clinical responses and improved survival in metastatic melanoma patients (Hodi F S, et al. N Engl J Med 2010; 363:711-23; Di Giacomo A, et al. Cancer Immunol Immunother 2011; 60:467-77). Based on its clinical activity the anti-CTLA-4 mAb ipilimumab (marketed under the name Yervoy®) has been approved by regulatory Agencies (FDA in 2011 and EMA in 2012) and is commercialized for the treatment of metastatic melanoma patients. Another anti-CTLA-4 mAb named tremelimumab is in clinical development in different solid tumors. Other immunotherapeutic mAb in clinical development are those that target the Programmed death 1 (PD-1) protein, a T-cell co-inhibitory receptor (Freeman G J et al. J Exp Med 2000; 192:1027-34), or its counter-receptors PDL-1 and PDL-2 (Dong et al. Nat Med 2002; 8:793-800; Latchman Y, et al. Nat Immunol 2001; 2:261-8). Blockade of the interactions between PD-1 and PDL-1/-2 mediates antitumor activities in preclinical models (Iwai Y et al., *Proc Natl Acad Sci USA* 2002; 99:12293-12297). In addition, early clinical trials are showing clinical activity of both anti-PD-1 and anti-PDL-1 mAb in patients with advanced cancers, including non-small-cell lung cancer, melanoma, and renal-cell cancer (Brahmer J R, et al. *N Engl J Med.* 2012 Jun. 2; Topalian S L, et al. *N Engl J Med.* 2012 Jun. 2). Initial clinical trials are investigating the clinical potential of immunomodulating mAb that target other cell surface molecules expressed on immune cells such as CD137, OX-40, CD40 in solid and hemopoietic human malignancies (Seminars in Oncology, 2010 37:429-547).

A new promising therapeutic approach for the treatment of cancer is represented by therapies targeting the BRAF/mitogen-activated protein kinase (MAPK) pathway (Flaherty K T Cancer 2010 Nov. 1; 116(21):4902-13). Mutations in BRAF have been detected in a variety of tumor types, with the highest incidence in melanoma (ranging from 27% to 70%) (Maldonado J L, et al. J Natl Cancer Inst 2003 Dec. 17; 95(24):1878-90). The identification of somatic mutations in BRAF, especially the V600E (Davies H, et al. Nature 2002 Jun. 27; 417(6892):949-54), led to the development of highly selective BRAF inhibitors, which provoke effects on proliferation and apoptosis only in cells harboring BRAF mutations (Flaherty K T Cancer 2010 Nov. 1; 116 (21):4902-13). Treatment with selective BRAF inhibitors resulted in a high initial response rate (ranging from 48% to 81%), but in a limited duration of response due to the development of resistance and disease progression. The molecular mechanisms of tumor resistance to BRAF inhibitors are being investigated, in order to develop therapeutic strategies for overcoming or preventing it. In colorectal cancer (CRC), the phosphoinositide3-kinase (PI3K)/AKT pathway is activated to a greater extent in $BRAF^{mut}$ CRC tumors, than in melanoma, and it is implicated in de novo and acquired resistance to BRAF inhibition (Mao et al Clin Cancer Res 2013; 19:657-667). PI3K inhibitors and demethylating agents (i.e., azacytidine) inhibit the PI3K pathway and synergize with BRAF inhibitors in growth inhibition of $BRAF^{mut}$ CRC cell line. Silencing of PTEN by methylation but also of other epigenetically-regulated proteins may account for the observed synergy (Mao et al Clin Cancer Res 2013; 19:657-667).

SUMMARY OF THE INVENTION

Building on the clinical efficacy of these new therapeutic tools, combinations with cytotoxic and targeted therapies, as well as with proteic vaccines are being investigated. Along this line, the authors took a completely different and new approach by investigating the clinical potential of immunomodulating monoclonal antibodies (mAb) as DHA. In fact, the authors reasoned that the demonstrated immunomodulatory potential of DHA could be effectively coupled with the anti-tumor action of immunomodulating mAb, thus comprehensively increasing the anti-tumor activity of each agent utilized alone. To provide experimental support to this hypothesis, the authors utilized a syngeneic murine cancer model to perform a pre-clinical evaluation of the anti-tumor activities of the DHA designated 5-aza-2'-deoxycytidine (5-AZA-CdR), administered in combination with different immunostimulatory mAb. A strong anti-tumor effect was induced by the combination therapy, and a direct involvement of host's immune response was demonstrated. The authors' in vivo evidences provide a strong scientific rationale for the development of new combined chemo (i.e., DHA)-immuno (i.e., immunomodulatory mAb) therapeutic approaches for cancer treatment. In addition, based on their immunomodulatory properties, novel combinations of DHA with other immunotherapeutic agents such as cancer vaccines, therapeutic cytokines, cellular therapies (including but not restricted to T cells, stem cells, dendritic cells, gene-modified and pharmacologically-modified immune and cancer cells) may generate more effective anti-cancer therapies.

Further, DHA represent a useful therapeutic strategy to overcome resistance to BRAF inhibitors (Mao et al Clin Cancer Res 2013; 19:657-667). The limited duration of response to selective BRAF inhibitors may be overcome by combining BRAF/MAPK-targeted agents with immunotherapy. Along this line, evidence showed that the BRAF inhibitor, Vemurafenib exerts potent effects on $BRAF^{mut}$ cancer cells, leading to improved antigen presentation and recognition by anti-tumor T cells that appear to be associated with the up-regulation of tumor antigens and different molecules involved in MHC class I antigen processing and presentation pathways (Donia et al Oncoimmunology 2012; 1:9, 1476-1483; Boni A, et al. Cancer Res 2010 Jul. 1; 70(13):5213-9). Thus, combinations of BRAF inhibitors with immunotherapy may be a rational direction to pursue in the melanoma therapy, in order to take advantage both of the rapid and high response rates of BRAF-inhibitors and of the long-lasting disease control of immunotherapeutic approaches (Boni A, et al. Cancer Res 2010 Jul. 1; 70(13): 5213-9). An alternative strategy will be to combine BRAF inhibitors with DHA and with other immunomodulatory agents described above.

It is therefore an object of the present invention a DNA hypomethylating agent and at least one immunomodulatory agent and/or optionally at least one targeted therapy agent for use in the treatment and/or in the prevention of cancer. Preferably, the DNA hypomethylating agent is selected from the group consisting of: 5-azacytidine [Vidaza], 5-aza-2'-deoxycytidine (5-AZA-CdR) [Dacogen], zebularine, procainamide, procaine, hydralazine, epigallocathechin-3-gallate, RG108, MG98. Still preferably, the immunomodulatory agent is selected from the group consisting of: immunomodulating antibody, cancer vaccine, therapeutic cytokine, cellular therapy. Yet preferably the immunomodulating antibody is selected from the group consisting of: an anti-CTLA-4, an anti-PDL-1, an anti-PDL-2, an anti-PD1, an anti-CD137, an anti-CD40, an anti-OX-40 antibody. In a preferred embodiment the cancer vaccine is selected from the group consisting of: anti-idiotypic antibodies (e.g., anti-GD2 (Louis M. Weiner, Lancet. 2009 Mar. 21; 373(9668): 1033-1040), anti-HMW-MAA (Mittelman A, Proc. Nati. Acad. Sci. USA Vol. 89, pp. 466-470, January 1992), inhibitors of angiogenesis (e.g., bevacizumab, itraconazole, suramine), Tumor Antigen (such as component of the Cancer Testis Antigen family (e.g., NY-ESO-1, MAGE-A1, MAGE-A3) specific peptides or recombinant proteins. In a still preferred embodiment the therapeutic cytokine is selected from the group consisting of: Leucomax GM-CSF, IL-2, IL-12, TNF α, IFN γ, IFN α. In a preferred embodiment the cellular therapy is selected from the group consisting of: T cells, stem cells, dendritic cells, gene- or pharmacologically-modified immune and/or cancer cells. In a preferred embodiment the targeted therapy agent is selected from the group consisting of: a MAP kinase pathway inhibitor or a WNT pathway inhibitor. Preferably the MAP kinase pathway inhibitor is selected from the group consisting of: a BRAF inhibitor, a MEK inhibitor, a PI3K inhibitor or a c-KIT inhibitor. Still preferably the BRAF inhibitor is selected from the group consisting of: GDC-0879 ((E)-5-[1-(2-Hydroxy-ethyl)-3-pyridin-4-yl-1H-pyrazol-4-yl]-indan-1-one oxime), PLX-4720 ((Propane-1-sulfonic acid [3-(5-chloro-1H-pyrrolo[2,3-b]pyridine-3-carbonyl)-2,4-difluoro-phenyl]-amide), Sorafenib Tosylate (4-{4-[3-(4-Chloro-3-methyl-phenyl)-ureido]-phenoxy}-pyridine-2-carboxylic acid methylamide tosylate), dabrafenib (N-{3-[5-(2-aminopyrimidin-4-yl)-2-tert-butyl-1,3-thiazol-4-yl]-2-fluorophenyl}-2,6-difluorobenzenesulfonamide) or LGX818 (Methyl [(2S)-1-{[4-(3-{5-chloro-2-fluoro-3-[(methylsulfonyl)amino] phenyl}-1-isopropyl-1H-pyrazol-4-yl)-2-pyrimidinyl] amino}-2-propanyl]carbamate). Yet preferably, the MEK inhibitor is selected from the group consisting in: GSK1120212 (N-(3-{3-Cyclopropyl-5-[(2-fluoro-4-iodo-phenyl)amino]-6,8-dimethyl-2,4,7-trioxo-3,4,6,7-tetrahydropyrido[4,3-d]pyrimidin-1(2H)-yl}phenyl)acetamide), selumetinib (6-(4-bromo-2-chloroanilino)-7-fluoro-N-(2-hydroxyethoxy)-3-methylbenzimidazole-5-carboxamide) or MEK162 (5-((4-bromo-2-fluorophenyl)amino)-4-fluoro-N-(2-hydroxyethoxy)-1-methyl-1H-benzo[d]imidazole-6-carboxamide). In a preferred embodiment the WNT pathway inhibitor is selected from the group consisting of: a beta catenin inhibitor or a frizzled inhibitor. Preferably the beta catenin inhibitor is selected from the group consisting of niclosamide (5-cloro-N-(2-cloro-4-nitrofenil)-2-idrossibenzamide), XAV-939 (3,5,7,8-Tetrahydro-2-[4-(trifluoromethyl)phenyl]-4H-thiopyrano[4,3-d]pyrimidin-4-one), FH 535 (2,5-Dichloro-N-(2-methyl-4-nitrophenyl)-benzenesulfonamide) or ICG 001 ((6S,9aS)-6-(4-hydroxybenzyl)-N-benzyl-8-(naphthalen-1-ylmethyl)-4,7-dioxo-hexahydro-2H-pyrazino[1,2-a]pyrimidine-1(6H)-carboxamide).

In a preferred embodiment the DNA hypomethylating agent is 5-AZA-CdR and the immunomodulating antibody is an anti-CTLA-4 and/or an anti-PDL-1 antibody.

In a preferred embodiment the cancer is caused by a solid or hematopoietic tumor. Preferably the tumour is breast cancer, skin cancer, bone cancer, prostate cancer, non-small cell lung cancer, leukemias, lymphomas, melanoma, epidermoid carcinomas, hepatocellular carcinoma squamous non-small cell lung adenocarcinoma, brain cancer, cancer of the larynx, pancreas, rectum, parathyroid, thyroid, adrenal, neural tissue, head and neck, colon, stomach, bronchi, and kidney cancer, basal cell carcinoma, squamous cell carcinoma of both ulcerating and papillary type, liver cancer, lung cancer, Ewing's sarcoma, myeloma, giant cell tumour, small-cell lung tumour, gallstones, islet cell tumour, primary brain tumour, acute and chronic lymphocytic and granulocytic tumours, metastatic skin carcinoma, osteo sarcoma, adenoma, hyperplasia, mucosal neuronms, intestinal ganglioneuromas, neuroblastoma, retinoblastoma, soft tissue sarcoma, malignant carcinoid, topical skin lesion, rhabdomyosarcoma, Kaposi's sarcoma, osteogenic sarcoma, renal cell tumour, adenocarcinoma, glioblastoma multiforma, hyperplastic corneal nerve tumour or ovarian tumour.

Most preferably the tumour is breast cancer. In a preferred embodiment the tumor is resistant or refractory to anti-tumor therapies, in particular to BRAF inhibitors.

In a preferred embodiment the DNA hypomethylating agent and the at least one immunomodulatory agent and/or optionally the least one targeted therapy agent are administered simultaneously or sequentially. The DNA hypomethylating agent may be administered before or after the at least one immunomodulatory agent and/or optionally the least one targeted therapy agent. It is a further object of the invention a pharmaceutical composition comprising a DNA hypomethylating agent and at least one immunomodulatory agent and/or optionally at least one targeted therapy agent as defined above for use in the treatment and/or in the prevention of cancer, as defined above.

It is a further object of the invention a kit comprising a DNA hypomethylating agent and at least one immunomodulatory agent and/or optionally at least one targeted therapy agent as defined above for use in the treatment and/or in the prevention of cancer wherein the DNA hypomethylating agent and the at least one immunomodulatory agent and/or optionally the at least one targeted therapy agent are in separated containers or in the same container.

It is a further object of the invention a method of treating and/or preventing cancer comprising administering an effective amount of a DNA hypomethylating agent and an effective amount of at least one immunomodulatory agent and/or optionally an effective amount of at least one targeted therapy agent. The agents being defined as above. Preferably the DNA hypomethylating agent is 5-AZA-CdR and the immunomodulatory agent is an anti-CTLA-4 and/or an anti-PDL-1 antibody.

In the present invention a DNA hypomethylating agent may be a compound able to inhibit DNA methyltransferase activity reversing aberrant hypermethylation of a multitude of genes, restoring their expression and functional activity (Sigalotti L et al. Epigenetic drugs as immunomodulators for combination therapies in solid tumors Pharmacol Ther. 2013 Dec. 30). An immunomodulatory agent is defined as a compound that induces or increases immunogenicity and immune recognition of cancer cells by host's immune system. In the present invention a targeted therapy agent is defined as compound that blocks the growth of cancer cells by interfering with specific targeted molecules needed for carcinogenesis and tumor growth. A Mitogen-activated protein kinase kinase (MEK) inhibitor (e.g., GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1 (2H)-yl}phenyl)acetamide), selumetinib (6-(4-bromo-2-chloroanilino)-7-fluoro-N-(2-hydroxyethoxy)-3-methylbenzimidazole-5-carboxamide), MEK162 (5-((4-bromo-2-fluorophenyl)amino)-4-fluoro-N-(2-hydroxyethoxy)-1-methyl-1H-benzo[d]imidazole-6-carboxamide)) is a chemical compound that inhibits Mitogen-activated protein kinase kinase enzymes. A Phosphoinositide 3-kinase (PI3K) inhibitor (e.g., Wortmannin (11-(acetyloxy)-1S,6bR,7,8,9aS,10,11R,11bR-octahydro-1-(methoxymethyl)-9a,11b-dimethyl-3H-furo[4,3,2-de]indeno[4,5-h]-2-benzopyran-3,6,9-trione), LY294002 (2-Morpholin-4-yl-8-phenylchromen-4-one), perifosine (1,1-Dimethylpiperidinium-4-yl octadecyl phosphate)) is a potential medical drug that functions by inhibiting a Phosphoinositide 3-kinase resulting in tumor suppression. A c-KIT inhibitor (e.g., nilotinib (4-methyl-N-[3-(4-methyl-1H-imidazol-1-yl)-5-(trifluoromethyl)phenyl]-3-[(4-pyridin-3-ylpyrimidin-2-yl)amino]benzamide), imatinib (4-[(4-methylpiperazin-1-yl)methyl]-N-(4-methyl-3-{[4-(pyridin-3-yl)pyrimidin-2-yl]amino}phenyl)benzamide)) is a compound that inhibits c-KIT, a tyrosine kinase enzyme, involved with the transduction and processing of many extracellular and intracellular signals including cell proliferation. Refractory or resistant cancer is defined as a cancer that does not respond to existing anticancer therapy or treatment (i.e., chemotherapy, radiation therapy, targeted therapies). Such existing therapies may be a chemotherapy drug including: Abitrexate (Methotrexate Injection), Abraxane (Paclitaxel Injection), Adcetris (Brentuximab Vedotin Injection), Adriamycin (Doxorubicin) Adrucil Injection (5-FU (fluorouracil)), Afinitor (Everolimus), Afinitor Disperz (Everolimus), Alimta (PEMETREXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase Erwinia chrysanthemi), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Margibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone).

Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer.

Targeted therapy may be enzyme inhibitors such as Tyrosine kinase inhibitors, mTOR inhibitors, Proteosome inhibitors, Growth factor inhibitors, Signal-transduction inhibitors, Multi-targeted kinase molecule which blocks many different enzymes. It may also be called a multikinase inhibitor. Some targeted therapies change proteins within the cancer cells and cause the cells to die. These are called apoptosis-inducing drugs. Targeted therapy included also angiogenesis inhibitors, working for instance by blocking vascular endothelial growth factor, also called VEGF. VEGF is a family of protein growth factors made by some tumors. The VEGF proteins can attach to the VEGF receptors of blood vessel cells. This causes new blood vessels to form around the tumors. Blocking this process prevents angiogenesis, which would form new blood vessels to feed tumors so they could grow.

In the present invention the term "effective amount" shall mean an amount which achieves a desired effect or therapeutic effect as such effect is understood by those of ordinary skill in the art. In the present invention, the DNA hypomethylating agent and the immunomodulatory agent may be administered simultaneously or sequentially and they may be administered with a targeted therapy agent that may replace the immunomodulatory agent.

Pharmaceutical compositions containing the DNA hypomethylating agent and the immunomodulatory agent and/or optionally the targeted therapy agent of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intramusclular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

The compounds are preferably formulated for parenteral administration, e.g., by bolus injection or continuous infusion. Formulations for injection may be presented in unit dosage form, e.g. j in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the compounds of the present invention can conveniently be delivered in the form of an aerosol spray using a pressurized pack or a nebulizer and a suitable propellant The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Other delivery systems such as liposomes and emulsions can also be used.

A therapeutically effective amount refers to an amount of compound effective to prevent, alleviate or ameliorate cancer symptoms. Determination of a therapeutically effective amount is well within the capability of those skilled in the art, especially in light of the disclosure herein.

For any compound used in the methods of the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

The amount of the composition that is administered will depend upon the parent molecule included therein. Generally, the amount used in the treatment methods is that amount which effectively achieves the desired therapeutic result in mammals. Naturally, the dosages of the various compounds can vary somewhat depending upon the compound, rate of in vivo hydrolysis, etc. In addition, the dosage, of course, can vary depending upon the dosage form and route of administration.

In particular, DNA hypomethylating agent and immunomodulatory agent administration should follow the current clinical guidelines. For instance the immunomodulatory agent may be administered as the commercialized immunotherapeutic mAb, ipilimumab.

In general, however, the DNA hypomethylating agent described herein can be administered in amounts ranging from about 0.1 to about 3000 $mg/m^2$, preferably from about 0.1 to 1500 $mg/m^2$, still preferably from 1 to about 1000 $mg/m^2$, yet preferably from 1 to about 500 $mg/m^2$, yet preferably from 1 to about 200 $mg/m^2$, yet preferably from 1 to about 100 $mg/m^2$, yet preferably from 10 to about 100 $mg/m^2$.

The immunomodulating antibody described herein can be administered in amounts ranging from about 0.1 to about 60 mg/kg and preferably from about 0.1 to about 20 mg/kg, still preferably from about 0.2 to about 10 mg/kg, yet preferably from about 0.6 to about 6 mg/kg. The range set forth above is illustrative and those skilled in the art will determine the optimal dosing of the compound selected based on clinical experience and the treatment indication. Moreover, the exact formulation, route of administration and dosage can be selected by the individual physician in view of the patient's condition and of the most effective route of administration (e.g., intravenous, subcutaneous, intradermal). Additionally, toxicity and therapeutic efficacy of the compounds described herein can be determined by standard pharmaceutical procedures in cell cultures or experimental animals using methods well-known in the art. In one embodiment, the treatment of the present invention includes administering the compounds described herein in an amount of from about 0.3 to about 6 mg/kg/dose to a mammal with a cancer.

Alternatively and preferably, the amounts of the compounds administered can be based on body surface of human or other mammals. Preferably, the amounts of the compounds described herein range from about 0.2 to about 25 $mg/m^2$ dose/body surface. Some preferred doses include one of the following: 1.25, 2.0, 2.5, 3.3, 5, 10, and 16.5 $mg/m^2$. Preferably, the amounts administered can range from about 1.25 to about 16.5 $mg/m^2$ body surface/dose. Alternatively, they can be from about 2.5 to about 13 $mg/m^2$ body surface/dose or from about 2 to about 5 $mg/m^2$ body surface/dose. The treatment protocol can be based on a single dose administered once every three weeks or divided into multiple doses which are given as part of a multi-week treatment protocol. Thus, the treatment regimens can include one dose every three weeks for each treatment cycle and, alternatively one dose weekly for three weeks followed by one week off for each cycle. The precise dose and schedule of administration will depend on the stage and severity of the condition, and the individual characteristics of the patient being treated, as well as the most effective biological activity of treatment as will be appreciated by one of ordinary skill in the art. It is also contemplated that the treatment continues until satisfactory results are observed, which can be as soon as after 1 cycle although from about 3 to about 6 cycles or more cycles may be required such as in a maintenance schedule of administration.

In some preferred embodiments, the treatment protocol includes administering the amount ranging from about 1.25 to about 16.5 $mg/m^2$ body surface/dose every three weeks repeating for about 3 cycles or more. The amount administered per each cycle can range more preferably from about 2.5 to about 16.5 $mg/m^2$ body surface/dose. Alternatively, the compounds described herein can be administered weekly for three weeks, followed by one week without treatment and repeating for about 3 cycles or more until the desired results are observed. It is contemplated that the treatment will be given for one or more cycles until the desired clinical and biological result is obtained. The exact amount, frequency and period of administration of the compound of the present invention will vary, of course, depending upon the sex, age and medical condition of the patient as well as the severity and type of the disease as determined by the attending clinician.

Still further aspects include combining the therapy described herein with other anticancer therapies for synergistic or additive benefit.

The schedule of treatment with the combinations can foresee that DHA is administered concomitantly, before and/or after any of the "partner" immunomodulatory agent (eg, immunomodulatory mAb, vaccines, etc, etc) identified above.

The dose of DHA and of the "partner" immunomodulatory agent (eg, immunomodulatory mAb, vaccines, etc, etc) identified above can cover a wide range of concentrations. Combination therapies can be utilized for advanced stage of disease but also, prospectively, in the adjuvant and neo-adjuvant setting.

BRIEF DESCRIPTION OF THE DRAWINGS

The present invention will be described by means of non-limiting examples in reference to the following figures.

FIG. 1. Anti-tumor activity of in vivo 5-AZA-CdR/anti-CTLA-4 mAb combination therapy. BALB/c mice were sc inoculated with $2\times10^5$ TS/A cells. Groups of mice were ip injected with anti-CTLA-4 mAb (triangle symbols ▲) on days 2, 5, 8; 5-AZA-CdR (diamond symbol ◊) on days 0, 7 and 42, 49 for the $2^{nd}$ cycle of treatment; 5-AZA-CdR (days 0, 7 and 42, 49 for the $2^{nd}$ cycle of treatment) and anti-CTLA-4 mAb (days 2, 5, 8 and days 44, 47, 50 for the $2^{nd}$ cycle of treatment) in combination (square symbol ■), or saline solution for control (x symbol). Tumor volumes (TV) from mice were measured periodically, all along the treatment, by using a caliper. and calculated as follows: TV=LD²/2 (in which L is the longest diameter and D the shortest one). Tumor mean values for each group are reported. Vertical arrows indicate days of different treatments. *, $p\leq0.05$; , $p\leq0.01$; *, $p\leq0.001$ vs. tumor volumes of control group. †, $p\leq0.05$; ††, $p\leq0.01$ vs. tumor volumes of 5-AZA-CdR group.

FIG. 2. Anti-tumor activity of in vivo 5-AZA-CdR/anti-PDL-1 mAb combination therapy. BALB/c mice were sc inoculated with $2\times10^5$ TS/A cells. Groups of mice were ip injected with anti-CTLA-4 mAb (triangle symbols ▲) on days 2, 5, 8; anti-PDL-1 mAb (solid circle symbol ●) on days 2, 5, 8; 5-AZA-CdR (solid diamond symbol ◆) on days 0 and 7; 5-AZA-CdR (on days 0 and 7) and anti-CTLA-4 mAb (on days 2, 5, 8) in combination (square symbol ■); 5-AZA-CdR (on days 0 and 7) and anti-PDL-1 mAb (on days 2, 5, 8) in combination (vertical line symbol ❘); or saline solution for control (x symbol). Tumor volumes (TV) from mice were measured periodically, all along the treatment, by using a caliper and calculated as follows: TV=LD²/2 (in which L is the longest diameter and D the shortest one). Tumor mean values for each group are reported. Vertical arrows indicate days of different treatments. *, $p\leq0.05$; **, $p\leq0.01$; vs. tumor volumes of control group.

FIG. 3. qMSP analysis of P1A-promoter methylation status. Genomic DNA, extracted one week after the end of the first cycle treatment (day 8) from tumors excised from mice treated with: saline solution, as control group (CTRL, from the left first bar), anti-CTLA-4 mAb (from the left, second bar), 5-AZA-CdR (from the left, third bar) and the combination of 5-AZA-CdR with anti-CTLA-4 mAb (last bar), was modified with sodium bisulfite. Real-time qMSP analyses of P1A promoter were performed on bisulfite-modified genomic DNA using methylated- or unmethylated-specific primer pairs. Data are reported as percentage of methylation that was defined as the ratio between methylated molecules and the sum of methylated and unmethylated molecules. Bars, SD; *, $p\leq0.05$ vs. control group.

FIG. 6. Role of immune response in anti-tumor activity of in vivo 5-AZA-CdR/anti-CTLA-4 mAb combination therapy. Athymic nude mice (A), SCID/Beige (B) and BALB/c (C) mice were sc inoculated with $2\times10^5$ TS/A cells. Groups of mice, for each strains, were ip injected with anti-CTLA-4 mAb (triangle symbols ▲) on days 2, 5, 8; 5-AZA-CdR (diamond symbol D) on days 0 and 7; 5-AZA-CdR (on days 0 and 7) and anti-CTLA-4 mAb (on days 2, 5, 8) (square symbol ■), or saline solution for control (x symbol). Tumor volumes (TV) from mice were measured periodically, all along the treatment, by using a caliper and calculated as follows: TV=LD²/2 (in which L is the longest diameter and D the shortest one). Tumor mean values for each group are reported. Vertical arrows indicate days of different treatments. *, $p\leq0.05$; **, $p\leq0.01$ vs. tumor volumes of control group.

DETAILED DESCRIPTION OF THE INVENTION

Methods

Cells and Animals

Primary cultures of murine mammary carcinoma cells TS/A were grown in DMEM Medium supplemented with 10% heat-inactivated FCS (Lonza), 2 mM L-glutamine (Biochrom AG) and 50 μM β-mercaptoethanol.

Six-week-old female BALB/c, athymic nude and SCID/Beige mice were obtained from Harlan laboratories (Udine, Italy). Animal care and use were in accordance with Institutional guidelines and the indications of Workman et al. (Workman P, et al. Br J Cancer. 2010 May 25; 102(11): 1555-1577).

Monoclonal Antibodies and Reagents

The monoclonal antibodies (mAb) 9H10, against CTLA-4 (Catalog #: BE0131) and 10F.9G2, against PDL-1 (Catalog #: BE0101), were purchased from BioXCell (West Lebanon, N.H., USA). 5-AZA-CdR (Catalog #: A3656) was purchased from Sigma Chemical Co. (St. Louis, Mo., USA).

Mice Treatment

Mice were sc injected in the flank region with TS/A cells ($2\times10^5$) resuspended in 0.1 ml of physiologic saline. Animals were examined daily and after a latency period of 1 week, mice bearing clearly palpable and visible tumor grafts (diameter≥0.2 cm) were ip injected with 0.2 ml/injection of i) 15 mg/kg/day of 5-AZA-CdR, three times a day every three hours on days 0 and 7 and on days 42 and 49 for the $2^{nd}$ cycle of treatment; ii) 100 μg/mouse of anti-CTLA-4 mAb, on days 2, 5 and 8 and on days 44, 47 and 50 for the $2^{nd}$ cycle of treatment; iii) 100 μg/mouse of anti-PDL-1 mAb on days 2, 5 and 8; iv) combined administration of 5-AZA-CdR and anti-CTLA-4 mAb according to the above reported schedules or; v) combined administration of 5-AZA-CdR and anti-PDL-1 mAb according to the above reported schedules. Control mice were ip injected with 0.2 ml of saline solution. Animals were weekly monitored for changes in the tumor size or sacrificed by $CO_2$ overdose; for the latter, tumor tissues were surgically removed, and each specimen, divided under sterile conditions, were snap-frozen in liquid nitrogen and stored at −80° C. until used for RNA and DNA extraction.

Figure 6:
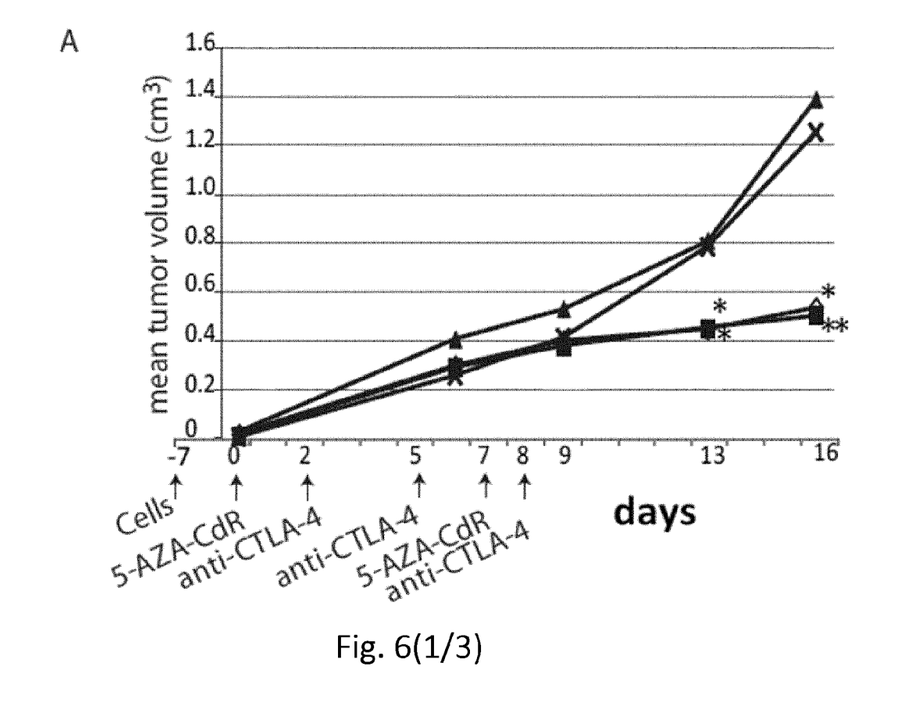

For experiments reported in FIG. 6, animals received using the same schedule and dose only the first treatment cycle up to day 8.

In Vivo Drug Tolerability and Antiproliferative Activity

In vivo tolerability was evaluated by measurements of body weight and mortality rate. The antiproliferative activity of the drug was evaluated by caliper measurements of tumor mass. Body weight and tumor size measurements were recorded periodically, all along the treatment. Tumor volumes (TV) were calculated as follows: $TV=LD^2/2$ (in which L is the longest diameter and D the shortest one).

RNA and DNA Extraction

RNA and DNA were extracted from tissues sections, removed from control and treated mice one week after the end of the first cycle treatment (day 8) and homogenized with the aid of Tissue Lyser II (QIAGEN) in Trizol reagent or lysis buffer, respectively. Total RNA was extracted following the manufacturer's instructions and stored at −80° C. Total genomic DNA was extracted by digestion with 100 μg/ml proteinase K in the presence of 0.5% SDS at 50° C. overnight, followed by phenol/chloroform extraction and ethanol precipitation. Genomic DNA was eluted in TE buffer and stored at −20° C.

RT-PCR Analysis

RT-PCR reactions were performed using oligonucleotide primer sequences and PCR amplification programs specific for P1A and Mage-a family (Coral S, Covre A et al, Br J Cancer. 2012 Sep. 25; 107(7):1116-24). The integrity of RNA and random primers-synthesized cDNA was confirmed by the amplification of all cDNA samples with β-actin-specific primers, as previously described (Coral S, Covre A et al, Br J Cancer. 2012 Sep. 25; 107(7):1116-24). Five μA of each RT-PCR sample were run on a 2% agarose gel and visualized by ethidium bromide staining.

Real-Time Quantitative RT-PCR Analysis

Real-time quantitative RT-PCR analyses were performed as previously described (Calabro L, et al., J Cell Physiol 2005; 202:474-7) Briefly, total RNA was digested with RNAse-free DNAse (Roche Diagnostics), to remove contaminating genomic DNA. Synthesis of cDNA was performed on 1 μg of total RNA using M-MLV reverse transcriptase (Invitrogen) and random hexamer primers (Promega), following manufacturers' instructions. Measurement of gene expression was performed utilizing the ABI prism 7000 Sequence Detection System (Applied Biosystems), as previously described (Calabro L, et al., J Cell Physiol 2005; 202:474-7). cDNA standards were obtained by RT-PCR amplification of the specific mRNAs and quantitated by NanoDrop® ND-1000 UV-Vis Spectrophotometer. SYBR Green quantitative RT-PCR reactions were performed on 10 ng retrotranscribed total RNA in a final volume of 25 μl 1× SYBR Green Master Mix (Applied Biosystems). The primers utilized for real-time RT-PCR assays were:

P1A, forward 5'-GGTGCCGGAGCTGAGGA-3' (SEQ ID No. 1) and reverse 5'-TAGACACCAGGAAATT-AGGGTCG-3' (SEQ ID No. 2); mouse ß-actin, forward 5'-ACCAGTTCGCCATGGATGAC-3' (SEQ ID No. 3) and reverse 5'-TGCCGGAGCCGTTGTC-3'(SEQ ID No. 4). The copy numbers of P1A and of the reference gene ß-actin were established in each sample by extrapolation of the standard curve. The number of P1A cDNA molecules in each sample was then normalized to the number of cDNA molecules of ß-actin.

Quantitative Methylation-Specific PCR (qMSP) Analyses

Bisulfite conversion was carried out on 500 ng genomic DNA using EZ DNA Methylation-Gold™ Kit (Zymo Research, Orange, Calif., USA), according to the manufacturer's protocol. Primers for the analysis of the methylation status of P1A, designed using the free on-line software MethPrimer (Li L C and Dahiya R Bioinformatics 2002; 18:1427-31), were: P1A (Methylated), forward 5'-TTAAGTGCGTTATTACGTTTGGTTTTTAC-3' (SEQ ID No. 5), reverse 5'-ATAACCGATTATTTAATA-CAAAAATCGACG-3' (SEQ ID No. 6); P1A (Unmethylated), forward 5'-GATTAAGTGTGTTAT-TATGTTTGGTTTTTAT-3' (SEQ ID No. 7), reverse 5'-ACATAACCAATTATTTAATACAAAAATCAACA-3' (SEQ ID No. 8). SYBR green qMSP reactions were performed on 2 μl of bisulfite-modified genomic DNA in a final volume of 25 μl 1× Power SYBR green mastermix (Applyed Biosystems) at 95° C. for 10 min, followed by 45 cycles of 15 sec at 95° C. and 1 min at 60° C., using methylated- or unmethylated-specific primer pairs. The copy number of methylated or unmethylated sequences for the target gene was established in each sample by extrapolation from the standard curves. The percentage of methylation was defined as the ratio between methylated molecules and the sum of methylated and unmethylated molecules.

Results

Combined Effect of 5-AZA-CdR and of Anti-CTLA-4 mAb on Tumor Growth

Figure 1:
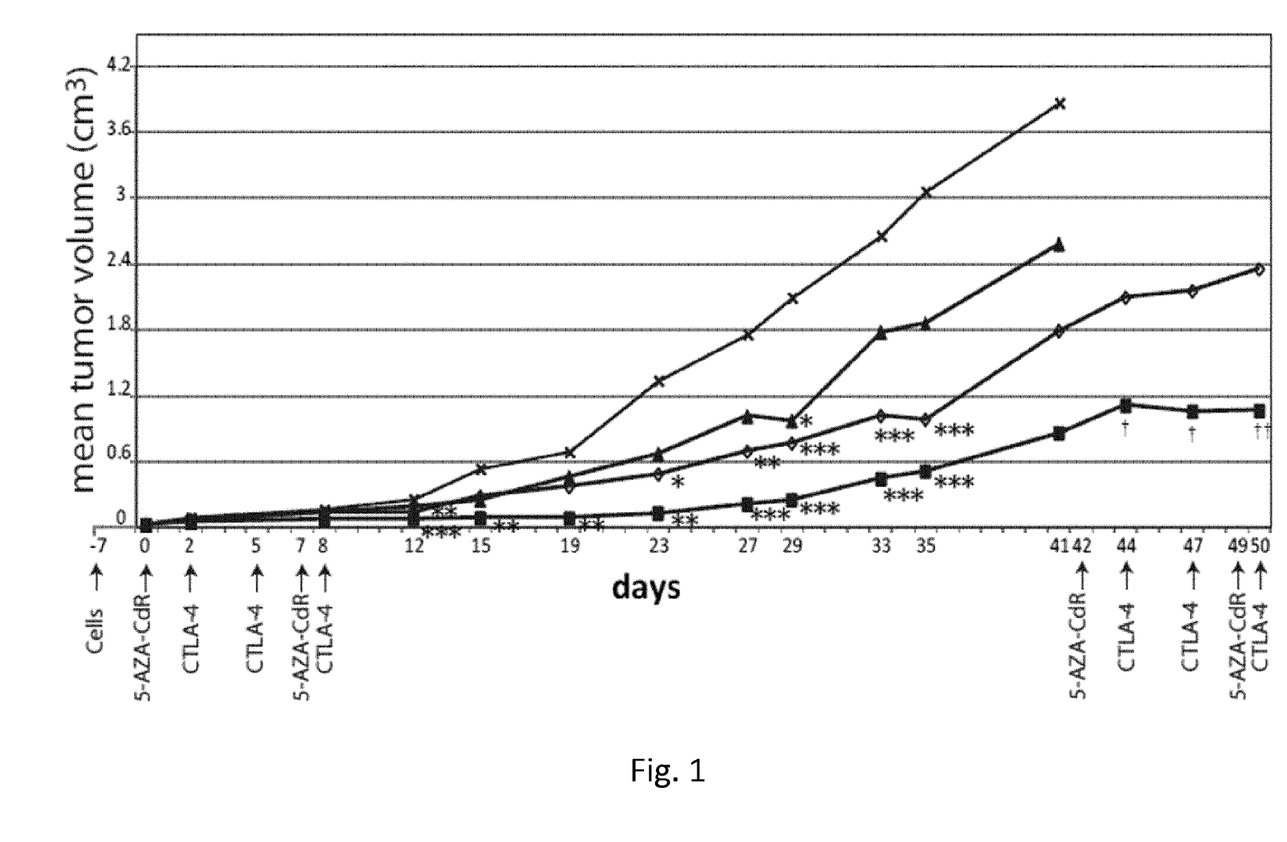

To address the anti-tumor activity of 5-AZA-CdR and of anti-CTLA-4 mAb, administered alone or in combination, TS/A cells were inoculated in syngeneic BALB/c mice that were then treated with 5-AZA-CdR either alone or in combination with anti-CTLA-4 mAb. Tumor volumes were monitored twice a week throughout the experiment (FIG. 1). From day 12, a scanty, not statistically significant, reduction of tumor growth was detected in mice treated with anti-CTLA-4 mAb alone, as compared to control mice, and remained evident (range: 33.1%-54.6%) at different investigated time-points throughout the study (FIG. 1). Equally, from day 12, 5-AZA-CdR-treated mice showed a tumor mass significantly (p values ranging from $p<0.05$ to $p<0.001$) smaller (range: 0.14 $cm^3$±0.05 to 1.80 $cm^3$±0.38), than that of control mice (range: 0.25 $cm^3$±0.05 to 3.87 $cm^3$+0.74), indicating a tumor growth inhibition ranging from 40.7% to 67.6% at days 15 and 35, respectively (FIG. 1). Noteworthy, the maximum anti-tumor effect was induced by the combined administration of 5-AZA-CdR and anti-CTLA-4 mAb. Indeed, a tumor mass significantly (p values ranging from $p<0.01$ to $p<0.001$) smaller (range: 0.08 $cm^3$±0.02 to 0.86 $cm^3$±0.31) was persistently observed in all investigated treated mice, as compared to control mice, indicating a tumor growth inhibition ranging from 77.6% to 89.4% at days 41 and 23, respectively (FIG. 1).

At day $41^{st}$ tumor diameters of control and anti-CTLA-4 mAb-treated mice exceeded the maximum standard parameters, thus, animals in these two groups were euthanized (Workman P, et al. *Br J Cancer.* 2010 May 25; 102(11): 1555-1577).

To evaluate the potential cumulative anti-tumor activity of repeated administrations of investigated therapies, mice from 5-AZA-CdR and from 5-AZA-CdR and anti-CTLA-4 mAb groups, were treated with a $2^{nd}$ cycle of treatment, at day $42^{nd}$. Noteworthy, a significant (p<0.05 and p<0.01) and persistent reduction of tumor growth was observed in mice treated with the combination of 5-AZA-CdR and anti-CTLA-4 mAb, whose tumor volumes ranged from 1.07 cm$^3$±0.43 to 1.11 cm$^3$±0.42, as compared to the tumor volumes from mice treated with 5-AZA-CdR alone (range: 2.10 cm$^3$±0.62 to 2.46 cm$^3$±0.32). The maintenance of body weight, for the duration of the treatment, in all investigated mice demonstrated the good tolerability of the investigated therapies (data not shown).

Combined Effect of 5-AZA-CdR and of Anti-PDL-1 mAb on Tumor Growth

Figure 2:
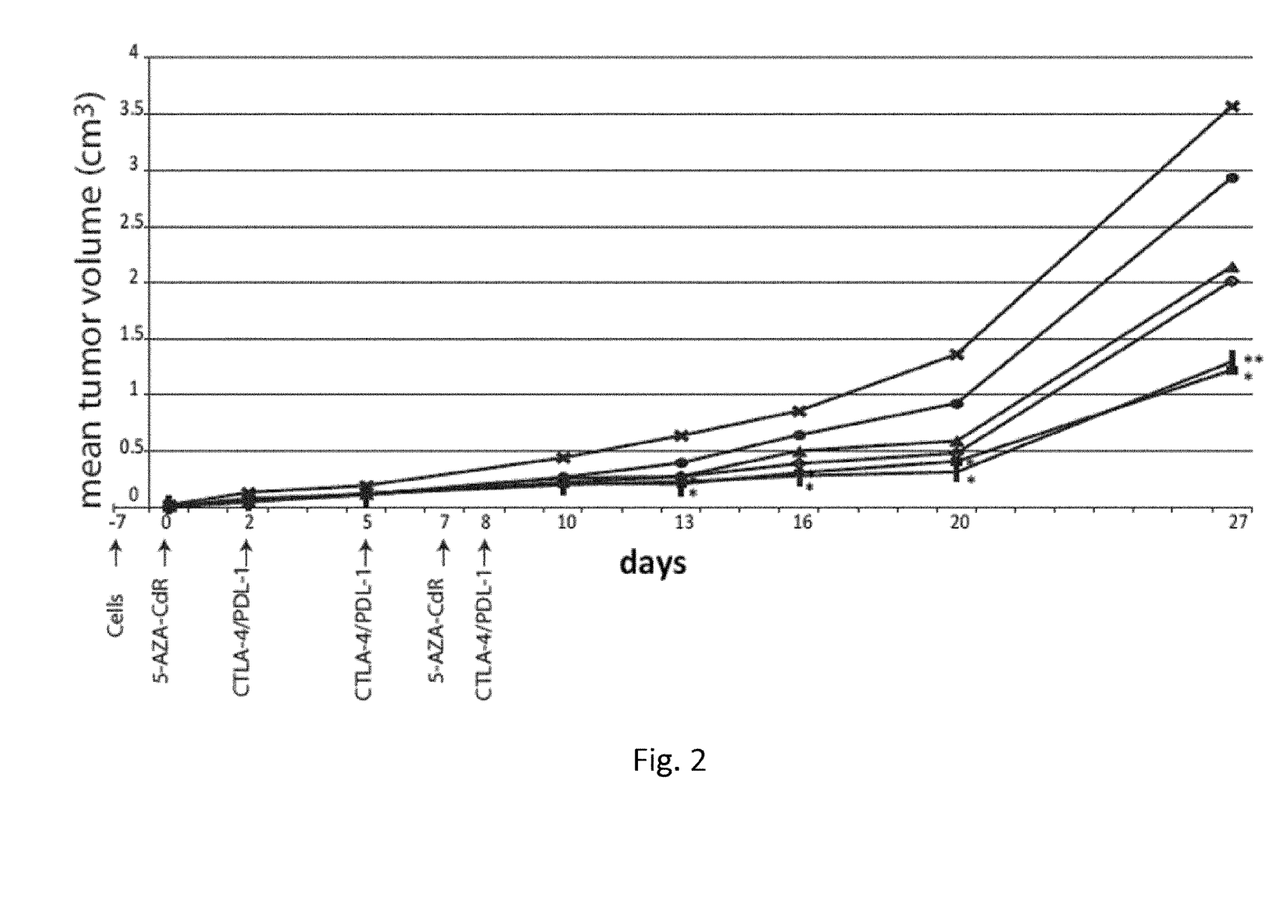

To further investigate the anti-tumor activity of 5-AZA-CdR in combination with other immunomodulating mAb, TS/A cells were inoculated in syngeneic BALB/c that were then treated with 5-AZA-CdR either alone or in combination with anti-PDL-1 mAb; the anti-CTLA-4 mAb was utilized as "reference" for its demonstrated (FIG. 1) anti-tumor activity when combined with DHA. Tumor volumes were monitored twice a week throughout the experiment (FIG. 2). As compared to control mice, the maximum anti-tumor effect was achieved in mice treated with 5-AZA-CdR combined with anti-PDL-1 mAb (range: 53.7-76.3%); noteworthy, this antiproliferative effect was similar to that observed utilizing 5-AZA-CdR in combination with anti-CTLA-4 mAb (range: 50.4-69.5%). Both regimens induced a significant (p<0.05 and p<0.01) reduction in tumor growth, as compared to control mice.

Immunomodulatory Activity of 5-AZA-CdR and/or Anti-CTLA-4 mAb in Tumor Tissues

Figure 3:
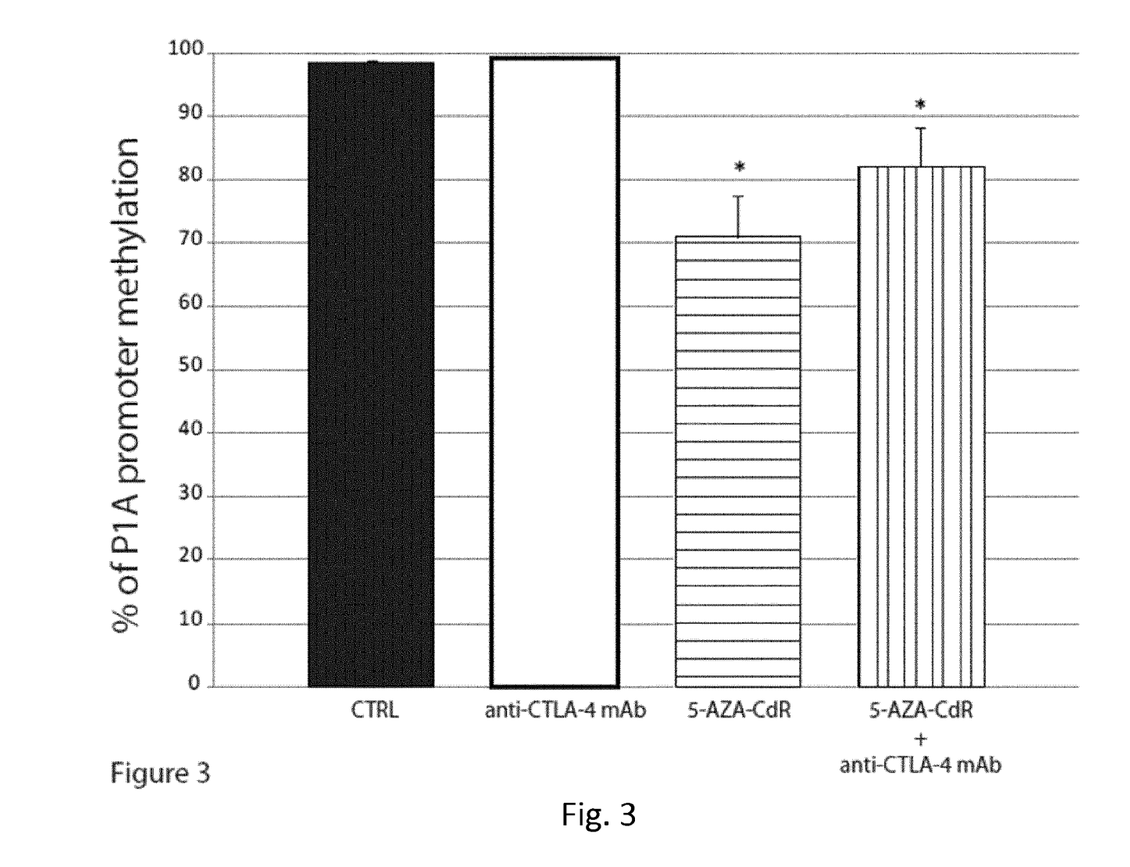
Figure 4:
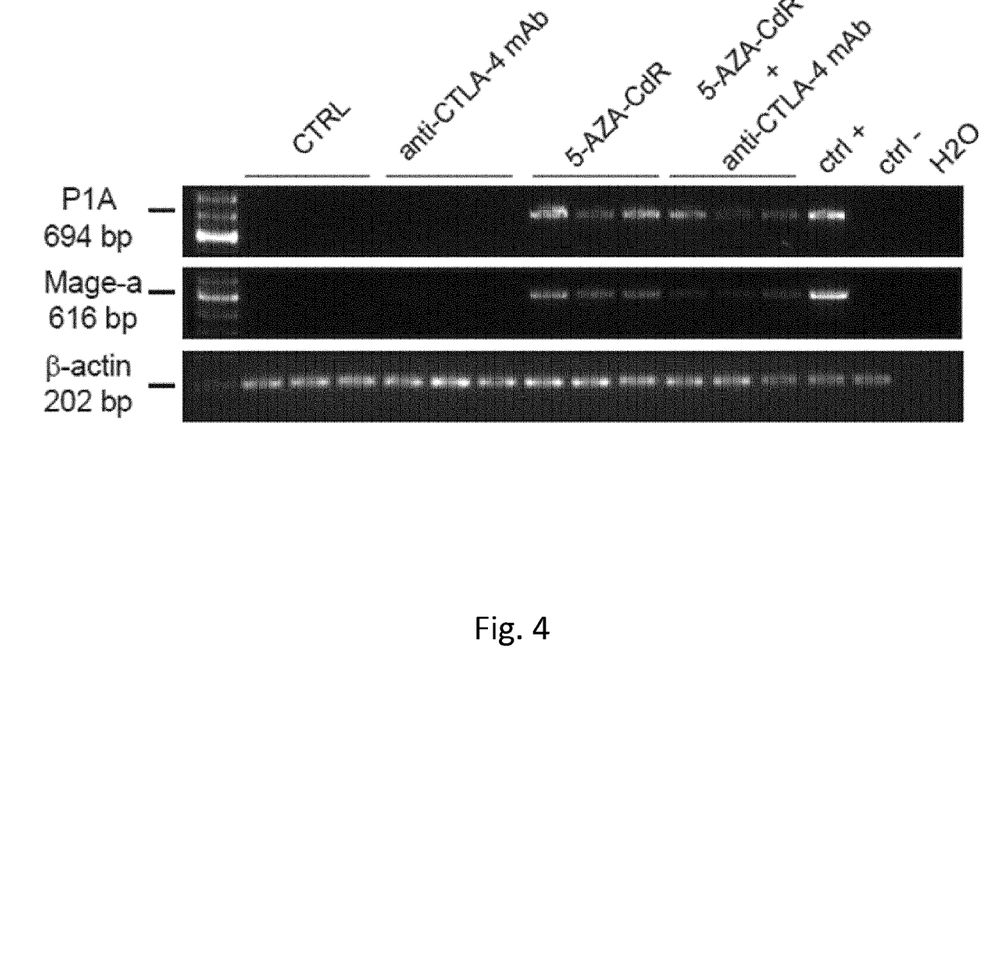
FIG. 4. RT-PCR analysis of murine CTA expression in tumor from control and treated mice. Total RNA was extracted one week after the end of the first cycle treatment (day 8) from tumors excised from mice treated with: saline solution, as control group (CTRL), anti-CTLA-4 mAb, 5-AZA-CdR and the combination of 5-AZA-CdR with anti-CTLA-4 mAb. Total RNA from mouse testis and splenocytes was utilized as positive control (ctrl +) or negative control (ctrl −), respectively. RT-PCR analysis was performed using primer pairs specific for murine CTA (i.e., P1A, or Mage-a family members) or β-actin. PCR products were then separated on a 2% agarose gel and visualized by ethidium bromide staining. Figure shows data from three representative mice out of six for control and treated groups.
Figure 5:
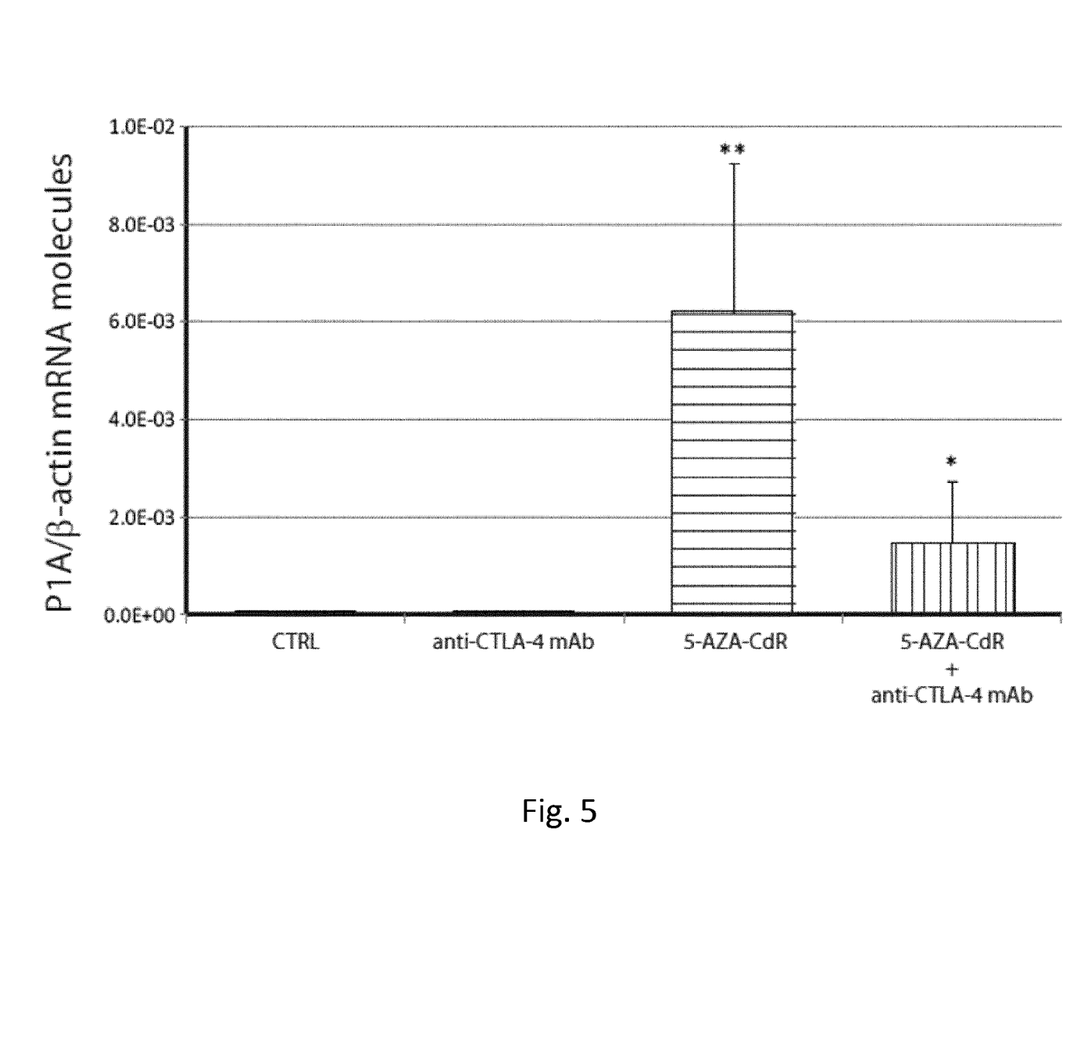
FIG. 5. Real-time quantitative RT-PCR analysis of P1A expression in tumor tissues excised from control and treated mice. Total RNA was extracted, one week after the end of the first cycle treatment (day 8), from tumors excised from control mice (from the left first bar) and mice treated with: anti-CTLA-4 mAb (from the left second bar), 5-AZA-CdR (from the left third bar) and the combination of 5-AZA-CdR with anti-CTLA-4 mAb (last bar). TaqMan quantitative RT-PCR reactions were performed on retrotranscribed total RNA, utilizing P1A- and β-actin-specific primers. CTA expression was normalized to the expression of the β-actin gene. Values are reported as P1A molecules/β-actin molecules, on a linear scale. Bars, SD; *, $p\leq0.05$; **, $p\leq0.01$ vs. control group.

To investigate the potential relative contribution of 5-AZA-CdR and of anti-CTLA-4 mAb in the modulation of the expression of given immune molecules on tumor tissues, BALB/c mice were inoculated with TS/A cells and treated with 5-AZA-CdR and/or anti-CTLA-4 mAb, according to the previously reported regimens. The DNA hypomethylating activity of DHA was investigated by qMSP analysis on genomic DNA from tumor tissues excised one week after the end of the first cycle treatment (day 8) from treated and control mice, by measuring changes induced in CpG dinucleotides located in the promoter region of P1A. As compared to control mice, a significant (p<0.05) reduction of the constitutive methylation levels of P1A promoter in cancer tissues from mice treated with 5-AZA-CdR alone or in combination with anti-CTLA-4 mAb was observed (FIG. 3). No reduction in the methylation of P1A promoter was observed in neoplastic lesions from mice treated with anti-CTLA-4 mAb alone (FIG. 3). RT-PCR and Real-Time quantitative RT-PCR analyses were performed to investigate the efficacy of treatments to induce and/or up-regulate different murine CTA (i.e., P1A, Mage-a family) in tumor tissues. A strong de novo expression of P1A and Mage-a members (FIG. 4) was observed only in tumor tissues excised from animals treated with 5-AZA-CdR alone or in combination with anti-CTLA-4 mAb. In addition, levels of P1A-specific mRNA expression detected in neoplastic tissues excised from mice treated with 5-AZA-CdR alone or in combination with anti-CTLA-4 mAb were similar (FIG. 5). Notably, the higher necrosis and the loss of tissue architecture, together with the large lymphocyte infiltration into the tumors from mice treated with 5-AZA-CdR and anti-CTLA-4 mAb, as compared to 5-AZA-CdR treatment (see section below Histology and immunohistochemistry of surgically-excised tumors from treated mice) could alter the optimal experimental conditions, accounting for the different levels of P1A-specific mRNA expression detected in neoplastic tissues following the combination therapy, as compared to 5-AZA-CdR monotherapy.

Anti-Tumor Activity of 5-AZA-CdR in Combination with Anti-CTLA-4 mAb in Immunodeficient Mice To determine the contribute of host's immune cells to mediate the anti-tumor effect elicited by 5-AZA-CdR combined with anti-CTLA-4 mAb, immunodeficient (i.e., T cell-deficient athymic nude mice (FIG. 6A), T-cell-, B-cell- and natural killer cell-deficient (SCID/Beige) (FIG. 6B)) and immunocompetent (i.e., BALB/c (FIG. 6C)) mice were grafted with TS/A cells and treated according to the previously utilized regimens.

The anti-CTLA-4 mAb did not impair tumor growth in T cell-deficient athymic nude mice (FIG. 6A) and in SCID/Beige mice (FIG. 6B). In contrast, 5-AZA-CdR alone significantly (p<0.05 and p<0.01) reduced tumor growth both in T cell-deficient athymic nude mice (FIG. 6A) and in SCID/Beige mice (FIG. 6B); noteworthy, no difference in the reduction of tumor growth was observed in immunocompromised mice treated with 5-AZA-CdR alone or in combination with anti-CTLA-4 mAb (FIG. 6 A, B). Concomitant treatment of immunocompetent mice led to results (FIG. 6C) similar to those previously obtained in independent experiments (FIGS. 1 and 2).

Up-Regulation of Major Histocompatibility Complex (MHC) Class I Antigens on Tumor Tissues by the Treatment with 5-AZA-CdR and Anti-CTLA-4 mAb Treatment with 5-AZA-CdR, but not with anti-CTLA-4 mAb, increases constitutive expression of MHC class I antigens on tumours of treated mice.

Histology and Immunohistochemistry of Surgically-Excised Tumors from Treated Mice The treatment with anti-CTLA-4 does not induce tumour necrosis and induces little lymphocyte infiltration into the tumour. Treatment with 5-AZA-CdR does not induce tumour necrosis neither induces lymphocyte infiltration into the tumour. By contrast, treatment with the combination of anti-CTLA-4 and 5-AZA-CdR induces massive tumour necrosis and large lymphocyte infiltration into the tumour.

Discussion

The present invention demonstrates that 5-AZA-CdR in combination with anti-CTLA-4 and/or anti-PDL-1 immunomodulating mAb induces a profound inhibition of tumor cell growth as compared to the agents utilized alone. These results may be generalized for any DNA hypomethylating agent because of their common effect in terms of DNA hypomethylation. Similarly, these results may be generalized for any immunomodulatory agent, in particular immunomodulating mAb that are all able to activate the immune system either by blocking inhibitory signals (e.g., anti-CTLA-4, anti-PD1, anti-PDL-1 and -2) or by delivering activating signals (e.g., anti-CD137, anti-CD40, anti-OX-40). DHA are able to modulate the immune phenotype (CTA, HLA class I antigens, co-stimulatory molecules and other immune molecules) in solid and hemopoietic tumors of different histotype. Therefore, the therapeutic combination of immunomodulating mAb and DHA is applicable across different human tumors. Experiments reported with immunodeficient mice indicate that host's immune cells and particularly T lymphocytes, but possible also other immune cells and antibodies, are necessary for the therapeutic efficacy of the combinations.

The invention claimed is:

1. A method of treating cancer comprising administering, to a patient in need thereof, an effective amount of 5-aza-2'-deoxycytidine (5-AZA-CdR) as a DNA hypomethylating agent, and at least one immunomodulating antibody; wherein the immunomodulating antibody is an anti-PDL-1, anti-PD1, anti-CD137, and/or an anti-OX-40 antibody.

2. The method according to claim 1, wherein the cancer is a hematopoietic tumor.

3. The method according to claim 2, wherein the hematopoietic tumor is resistant or refractory to at least one anti-tumor therapy.

4. The method according to claim 1, wherein the at least one immunomodulating antibody is an anti-PD1 antibody.

5. The method according to claim 1, wherein the at least one immunomodulating antibody is an anti-PDL-1 antibody.

6. The method according to claim 1, wherein the DNA hypomethylating agent and the at least one immunomodulating antibody are administered simultaneously.

7. The method according to claim 1, wherein the DNA hypomethylating agent and the at least one immunomodulating antibody are administered sequentially.

8. The method according to claim 1, wherein the cancer is a breast cancer.

9. The method according to claim 1, wherein the immunomodulating antibody is an anti-CD137 antibody.

10. The method according to claim 1, wherein the immunomodulating antibody is an anti-OX-40 antibody.

11. The method according to claim 1, wherein the cancer is a solid tumor.

12. The method according to claim 11, wherein the solid tumor is resistant or refractory to at least one anti-tumor therapy.

13. The method according to claim 11, wherein the method induces lymphocyte infiltration in a solid tumor in the patient.

14. The method according to claim 1, further comprising administering at least one targeted therapy agent.

15. The method according to claim 14, wherein the at least one targeted therapy agent is a MAP kinase pathway inhibitor or a WNT pathway inhibitor.

16. The method according to claim 15, wherein the WNT pathway inhibitor is a beta catenin inhibitor or a frizzled inhibitor.

17. The method according to claim 16, wherein the beta catenin inhibitor is selected from the group consisting of niclosamide, XAV-939, FH 535 and ICG 001.

18. The method according to claim 15, wherein the MAP kinase pathway inhibitor is selected from the group consisting of a BRAF inhibitor, a MEK inhibitor, a PI3K inhibitor and a c-KIT inhibitor.

19. The method according to claim 18, wherein the BRAF inhibitor is selected from the group consisting of GDC-0879, PLX-4720, Sorafenib Tosylate, dabrafenib and LGX818.

20. The method according to claim 18, wherein the MEK inhibitor is selected from the group consisting of GSK1120212, selumetinib and MEK162.

21. The method according to claim 14, wherein the DNA hypomethylating agent and the at least one immunomodulating antibody and/or the at least one targeted therapy agent are administered simultaneously.

22. The method according to claim 14, wherein the DNA hypomethylating agent, the at least one immunomodulating antibody, and the at least one targeted therapy agent, are administered sequentially.

23. The method according to claim 14, wherein the cancer is a hematopoietic tumor.

24. The method according to claim 23, wherein the hematopoietic tumor is resistant or refractory to at least one anti-tumor therapy.

25. The method according to claim 14, wherein the cancer is a solid tumor.

26. The method according to claim 25, wherein the solid tumor is resistant or refractory to at least one anti-tumor therapy.

* * * * *